United States Patent
Nisch et al.

(10) Patent No.: US 6,347,250 B1
(45) Date of Patent: Feb. 12, 2002

(54) OPTICALLY CONTROLLABLE MICROELECTRODE ARRAY FOR STIMULATING CELLS WITHIN A TISSUE

(76) Inventors: Wilfried Nisch, Bismarckstrasse 20, D-72072 Tübingen; Martin Stelzle, Adolf-Damaschke-Strasse 47, D-72770 Reutlingen; Stefan Weiss, Jahnstrasse 15, D-72070 Tübingen; Eberhart Zrenner, Jasminweg 23, D-72076 Tübingen; Elke Günther, Steinenbergstrasse 34, D-74762 Reutlingen; Alfred Stett, Kniebisstrasse 40, D-72768 Reutlingen; Heinz Gerhard Graf, Im Dobel 10, D-71106 Magstadt; Michael Graf, Christofstrasse 42, D-71332 Waiblingen; Markus B. Schubert, Stäudach 26, D-72074 Tübingen; Harald N. Wanka, Ina-Seidel-Strasse 14, D-73630 Remshalden/Geradstetten; Anke Hierzenberger, Brandenkopfweg 10, D-71067 Sindelfingen, all of (DE)

( * ) Notice: Subject to any disclaimer, the term of this patent is extended or adjusted under 35 U.S.C. 154(b) by 0 days.

(21) Appl. No.: 09/298,816

(22) Filed: Apr. 23, 1999

Related U.S. Application Data

(63) Continuation-in-part of application No. PCT/EP97/05701, filed on Oct. 16, 1997.

(30) Foreign Application Priority Data

Oct. 23, 1996 (DE) .......................................... 196 44 113
Feb. 17, 1997 (DE) .......................................... 197 05 987

(51) Int. Cl.[7] ................................................ A61N 1/36
(52) U.S. Cl. ........................................................ 607/54
(58) Field of Search .............................. 607/53, 54, 116

(56) References Cited

U.S. PATENT DOCUMENTS

| 4,628,933 A | * 12/1986 | Michelson ..................... 607/54 |
| 5,397,350 A | 3/1995 | Chow et al. .................... 623/4 |
| 5,476,494 A | * 12/1995 | Edell et al. ..................... 607/54 |
| 5,895,415 A | * 4/1999 | Chow et al. .................... 607/54 |

FOREIGN PATENT DOCUMENTS

| DE | 44 24 753 A1 | 1/1996 | ............. A61F/2/16 |
| EP | 0 460 320 A2 | 8/1990 | ......... H01L/27/146 |
| WO | WO94/26209 | 11/1994 | ............. A61F/2/16 |

OTHER PUBLICATIONS

Wyatt, J and Rizzo, J, "Ocular Implants For The Blind" Bioelectronic Vision, *Spectrum* (May 1996) pp. 47, 50–53, 68–69.

* cited by examiner

*Primary Examiner*—William E. Kamm

(57) ABSTRACT

An optically controllable microelectrode array for stimulating cells within a tissue is disclosed. The array comprises a substrate having a surface. The substrate is adapted to be placed on the tissue with the surface adjoining the cells. The substrate further comprises a plurality of electrodes on the surface in contact with the cells for stimulating the cells. The electrodes are dimensioned such that a first surface area on the electrodes in contact with the cells is essentially smaller than a second surface area on the cells in which the cells may be contacted by the electrodes. An electrical stimulus is exerted from the electrodes to the cells under the control of light impinging on the tissue.

19 Claims, 2 Drawing Sheets

OPTICALLY CONTROLLABLE MICROELECTRODE ARRAY FOR STIMULATING CELLS WITHIN A TISSUE

This application is a Continuation-in-Part of International Application No. PCT/EP97/05701, filed Oct. 16, 1997, German Patent No. 197 05 987.2, filed Feb. 17, 1997, and German Patent No. 196 44 113.7, filed Oct. 23, 1996.

FIELD OF THE INVENTION

The present invention relates to the field of optically controllable microelectrode arrays for stimulating cells within a tissue. Still more specifically, the invention relates to an array having a substrate with a surface. The substrate is adapted to be placed on the tissue with the surface adjoining the cells. The substrate further comprises a plurality of electrodes on the surface in contact with the cells for stimulating same. An electrical stimulus is exerted from the electrodes to the cells under the control of light impinging on the tissue.

BACKGROUND OF THE INVENTION

European published patent application 0 460 320 discloses a subretinal implant adapted to be implanted into the lower layers of the retina. The prior art implant essentially consists of a silicon chip being configured by a large number of densely packed microphotodiodes. The photoactive surface of the photodiodes is directed towards the light impinging on the eye. The photodiodes generate an amplitude-modulated current stimulating the retinal cell layer lying on the implant surface. In such a way it shall be possible to enable patients suffering from various forms of retinal degeneration to improve or even reestablish vision.

In an earlier unpublished approach it has been suggested to use a specific microelectrode array for general applications. Within this approach biological cells in networks should be electrically stimulated. For that purpose one has used a plurality of microelectrodes. Each microelectrode comprises a contact electrode being adapted to be brought in electrical contact with the network of biological cells. Further, a connecting electrode is provided that is electrically connected with a measuring instrument or the like. Finally, a light sensitive element is used located between the contact electrode and the connector electrode. A preferred field of application of such arrays is the field of retina implants, however, the earlier approach is also adapted to be used for stimulating electrogenic cells "in vivo", for example in connection with cardiac pacers, muscle cell stimulators, bladder stimulators, wherein an optical light control, in particular by means of infrared light, may be effected through the skin.

In this prior approach the individual microelectrodes are optically controlled. As explained at the outset, such a structure may be used for generating electrical stimuli corresponding to image points on a retina.

Insofar it is of no importance whether the implant is a subretinal implant being implanted between lower layers of the retina or an epiretinal implant being placed on the front side of the retina.

In the prior art approaches the electrodes are configured as "microelectrodes", however, the actual dimensions of such microelectrodes are limited by the particularly manufacturing method used.

In prior art microelectrode arrays one has used microelectrodes with a diameter in the order of 10 $\mu$m. Hence, the surface portion of such microelectrodes that is available for making an electrical contact to a cell is in the same order of magnitude as the size of the cell itself.

With such configurations the cell will normally not be placed centrically on the respective electrode so as to entirely cover same. Instead, the cell will normally be offset with respect to the electrode so that only a portion of its entire surface that could be used for making contact will overlap with the corresponding contact surface of the microelectrode. However, this results in losses because the "free" surface portion of the microelectrode being not in contact with the cell will emit a current into the electrolyte of the retina which, however, does not generate a stimulus but will short-circuit the microelectrode instead.

It is, therefore, an object underlying the invention to improve an array of the kind mentioned at the outset such that the energy being available for generating stimuli is almost completely transmitted to the cells of the tissue.

SUMMARY OF THE INVENTION

These and other objects of the invention are solved in that the electrodes are dimensioned such that a first surface area on the electrodes in contact with the cells is essentially smaller than a second surface area on the cells in which the cells may be contacted by the electrodes.

The object underlying the invention is thus entirely solved. If, in simple words, the microelectrodes are made substantially smaller then the cells within the tissue, it is highly unlikely that the microelectrode will only partially be covered by the cell. Instead, in most cases the much bigger cell will completely cover several of the much smaller microelectrodes. If that is the case these electrodes may transmit their stimulus exclusively and completely to the cell but not to the surrounding electrolyte.

In a preferred embodiment of the array according to the invention the ratio between the second surface area and the first surface area is between 5 and 10.

This measure has the advantage that the effect described before may be achieved for dimensions of electrodes that may be realized with manufacturing methods available today.

In a particularly preferred embodiment of the invention the electrodes are arranged on the substrate surface in the geometrically densest possible arrangement, however, electrically isolated from each other.

This measure has the advantage that the cells may come in contact with the electrodes with their entire surface. For, if the electrodes are electrically isolated from each other and are packed as dense as geometrically possible, the electrodes are configured as a layer on the array surface and have a lateral conductivity being almost zero.

In another embodiment of the invention the electrodes are formed on the substrate by way of lithography.

For particularly small dimensions of the electrodes other methods may be considered. In particular, it is preferred to manufacture the electrodes through local crystallization within a layer of the substrate. The electrodes are, for example, configured by crystal nuclei organizing themselves on the substrate surface.

Likewise various configurations of such electrodes may be manufactured in very thin amorphous layers, for example from hydrogenized silicon (a-Si:H) by combined application of metal-induced crystallization and selective etching.

If the substrate layer itself is, for example, a P-layer and the lateral conductivity is set to be very small, then the layer configured by the electrodes themselves may be utilized as a part of a semiconductor switch or a microphotodiode.

It is particularly preferred when the electrodes are a part of a light-controlled switch by means of which a voltage may be applied as a local stimulus to a cell This measure has the advantage that the stimulating process as such may be exclusively triggered by an optical signal. This is of particular importance in connection with retina implants because the image impinging on the retina has both bright and dark portions. Hence, a switching and stimulation is effected within the bright areas whereas in the dark areas a stimulation is suppressed and the corresponding switches remain in their closed state.

As already indicated, it is preferred that the switch is configured by a plurality of substrate layers and the electrodes.

This has the advantage that the entire array is configured extremely small and thin when the layer configured by the electrodes itself is a layer of the semiconductor switch or the microphotodiode.

As already mentioned above, implants of the kind of interest may be utilized as subretinal implants or as epiretinal implants. In the latter case one must make sure that the implant itself is essentially permeable for visible light.

Further advantages will become apparent from the description and the enclosed drawing.

It goes without saying that the features specified before and those that will be explained hereinafter may not only be used in the particularly given combination but also in other combinations or alone without leaving the scope of the present invention.

BRIEF DESCRIPTION OF THE DRAWINGS

Embodiments of the invention are shown in the drawing and will be described in further detail within the subsequent description of the preferred embodiment.

DETAILED DESCRIPTION OF THE PREFERRED EMBODIMENT

Figure 1:
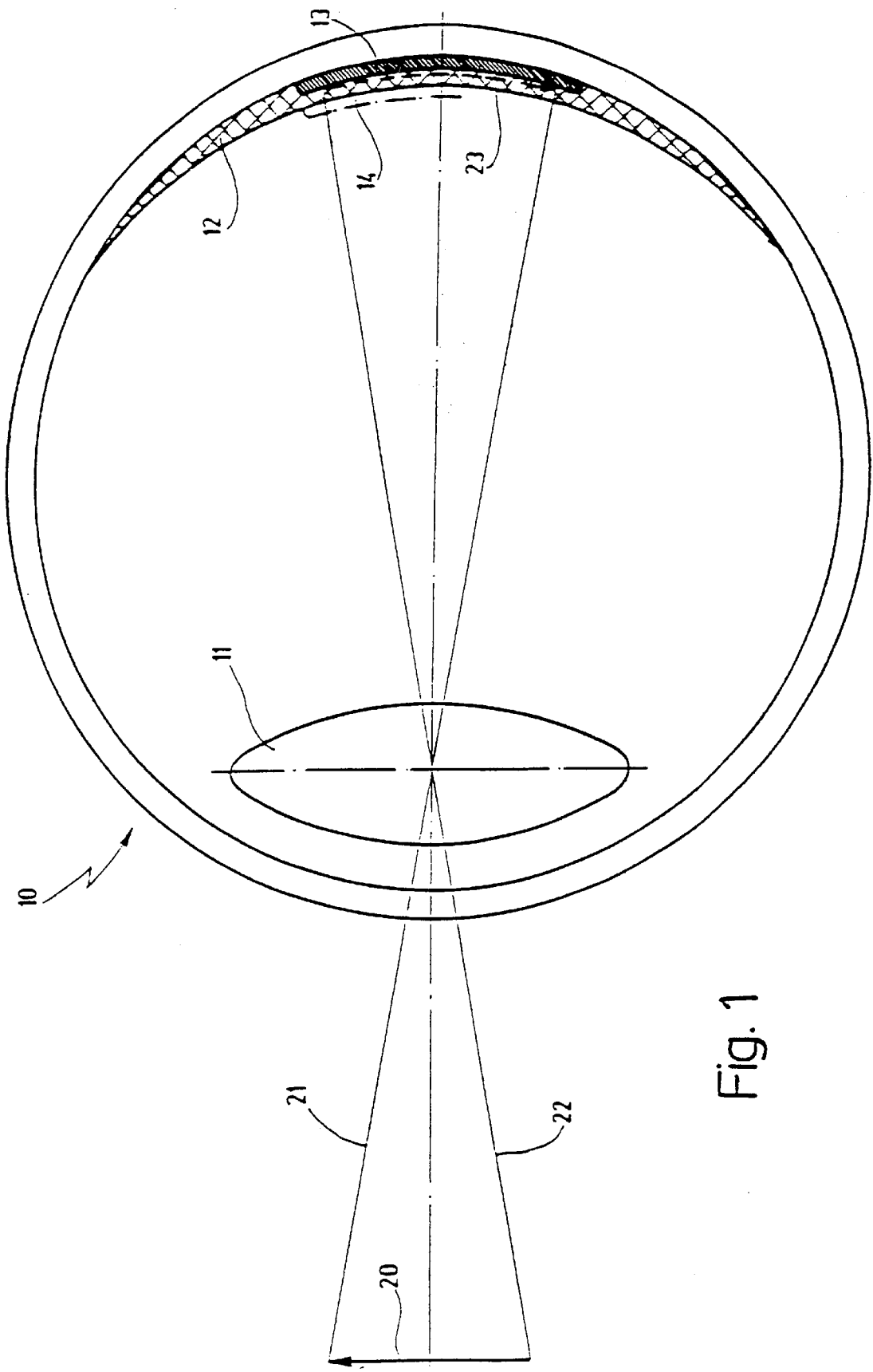
FIG. 1 shows an extremely schematic cross section through an eye wherein an implant utilizing an array according to the present invention is inserted into the retina.

In FIG. 1 reference numeral 10 as a whole indicates an eye, for example a human eye. Within eye 10 a lens 11 and a retina 12 are indicated.

A subretinal implant is shown at 13. Implant 13 is located within lower layers of retina 12. An epiretinal implant is indicated in dash-dot lines at 14 where it is placed on the retinal surface.

An object 20 is imaged in the usual fashion through lens 11 onto retina 12, as indicated with rays 21, 22 and an upside down image 23.

Figure 2:
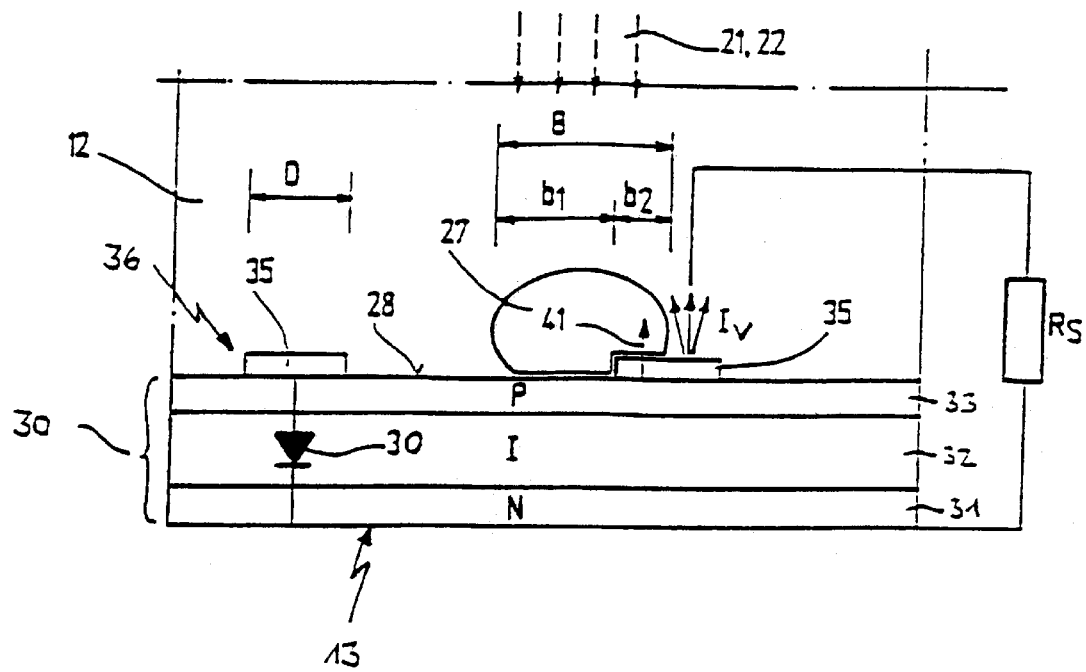
FIG. 2 shows a lateral cross-sectional view through a part of an implant in a subretinal arrangement, on a highly enlarged scale according to the prior art.

FIG. 2 shows a cross-sectional view through an implant on a highly enlarged scale.

Implant 13 in the depiction of FIG. 2 is implanted in a subretinal location, i.e. it is located beneath retina 12.

Within retina 12 a cell is indicated at 27. Cell 27 lies on a surface 28 of implant 13 and may be contacted there.

Implant 13 has a layered structure comprising a diode 30. Diode 30, for example, consists of an N-layer 31, with an I-layer 32 thereon plus an upper P-layer 33. Diode 30, however, may also have another structure, for example (in an upward direction) N-I-P or it may also have additional layers. Further, one may use P-N- or N-P-structures from crystalline silicon.

Two electrodes 35 are indicated on P-layer 33, i.e. on top of surface 28. Electrodes 35 are a part of a light-controlled elctronic switch being indicated as a whole at 36. Electrodes 35 establish a contact between cells 27 and microphotodiodes 30.

The light-controlled electronic switch 36 may comprise a contact electrode that is in contact with a network of biological cells, a connector electrode that is electrically connected with a measuring instrument or the like, and a layer-shaped light-sensitive element between the contact electrode and the connector electrode. The contact electrode and/or the light-sensitive element and/or the connector electrode may be configured as thin film elements.

As one can see from FIG. 2 electrodes 35 have a surface being indicated with a diameter D.

Diameter D is in the same order of magnitude as the width B of cell 27 which, in practice, is in the order of 10 $\mu$m.

Cell 27 shown in FIG. 2, however, covers electrode 35 only partially, i.e. with a partial area $b_2$, whereas a larger partial area $b_1$ of the surface of cell 27 lies on P-layer 33, i.e. is not connected to contact 35.

If, as indicated at 21, 22 in FIG. 2, visible light impinges on the optically controllable switch beneath electrode 35 shown on the right hand side, a stimulus 41 is triggered, however, stimulus 41 constitutes just a portion of the delivered energy. Another portion of the photocurrent, indicated in FIG. 2 at $I_V$, is lost and flows from the free surface of electrode 35 via the electrolyte back into the common or isolated reference area of implant 13, as indicated with a resistance $R_S$.

Figure 3:
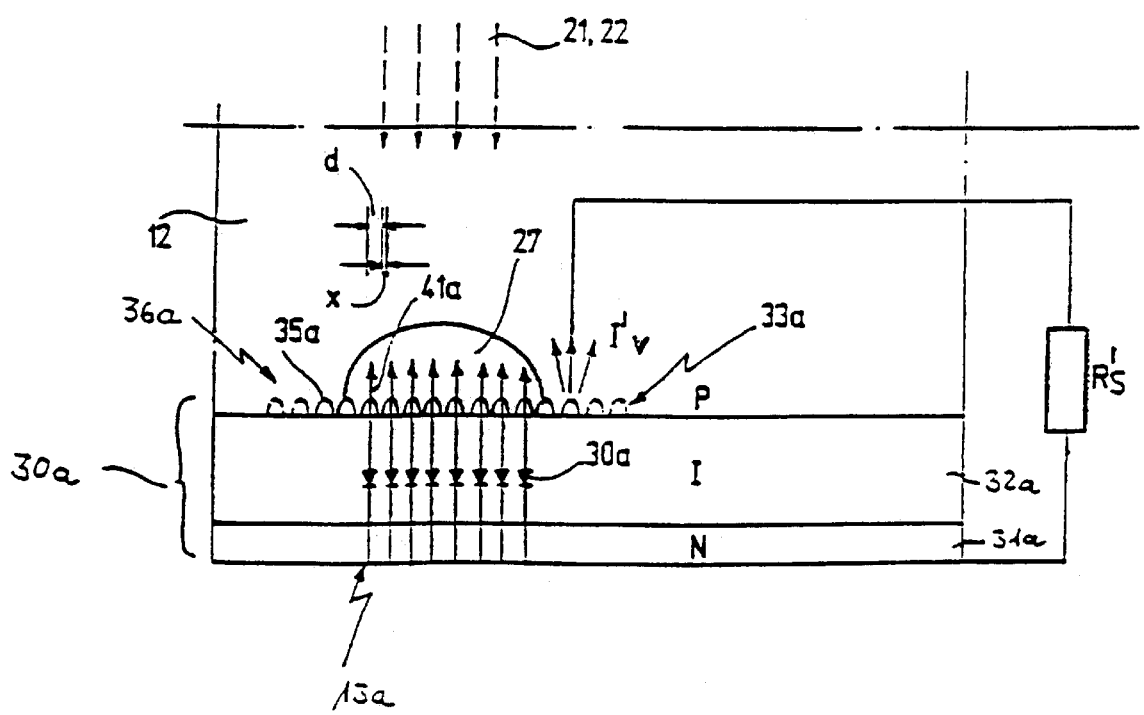
FIG. 3 shows a depiction, similar to that of FIG. 2, however, for a preferred embodiment of the present invention.

In order to avoid the disadvantages of the energy loss or in order to at least reduce same substantially, the arrangement may be modified, as shown in FIG. 3.

In FIG. 3 the electrodes 35a are configured substantially smaller. Their diameter d is now essentially smaller than the diameter D of FIG. 2. It may, for example, be just one fifth or one tenth of diameter D. Electrodes 35a, further, are offset from each other by a small distance x or are separated from each other by means of isolating layers so that they are electrically isolated from each other. In other words the layer 33a configured by electrodes 35a has a lateral conductivity being practically zero. Likewise layer 32a has an extremely small lateral conductivity.

Each of the electrodes 35a corresponds to a respective switch 36a, as also shown in FIG. 3.

The small electrodes 35a may either be manufactured by conventional lithographical methods; if extremely small dimensions are desired, it may be preferred to manufacture electrodes 35a with self-organizing principles, by configuring same as crystal nuclei in a substrate layer 33a. Substrate layer 33a may be a P-layer, as also indicated in FIG. 3. If that is the case the entire layer 33 shown in FIG. 2 as a P-layer may be deleted.

As one can clearly see from FIG. 3, the entire lower surface of cell 27 (disregarding the very small gaps between the electrodes 35a) is contacted by the electrodes 35a. If each of these small electrodes 35a transmits a stimulus 41a, the global stimulation of cell 27 is substantially larger as compared with the arrangement of FIG. 2.

If, in the configuration of FIG. 3, visible light impinges on electrodes 35a which are not covered by a cell 27, a lost current $I_v'$ is also generated. However, in contrast to the situation of FIG. 2 the entire light passing through a cell 27 is converted into stimuli so that the yield is substantially improved.

Implant 13 or 13a may be a subretinal or epiretinal implant. In the latter case it is necessary to configure layers 30 through 32 or 33 as being essentially permeable for visible light. However, implant 13 may also be used for other medical or biological applications as outlined in the introductory portion of the description. In particular, the small electrode approach may be utilized for general-purpose microphotodiode applications in the investigation of tissues both in biology and in neurology.

What is claimed is:

1. An optically controllable microelectrode array for stimulating cells within a tissue, the array comprising
   a substrate including at least one light-sensitive layer having a surface for facing a tissue to be stimulated, illuminated portions of said light-sensitive layer being adapted to switch to a stimulating potential when irradiated with light; and
   a plurality of electrodes arranged on said surface and adapted for contact with cells forming said tissue;
   wherein each said electrode is operative to cause said stimulating potential to electrically stimulate one or more cells in contact therewith when the electrode and the underlying substrate are irradiated with light.

2. The array of claim 1, wherein said electrodes are arranged on said surface and are electrically isolated from each other.

3. The array of claim 2, wherein said electrodes are formed on said substrate by way of lithography.

4. The array of claim 2, wherein said electrodes are formed by local crystallization within said substrate.

5. The array of claim 1, wherein said electrodes are a part of a switch, said switch being adapted to feed a stimulus to said cell.

6. The array of claim 5, wherein said switch is configured by a plurality of substrate layers and said electrodes.

7. The array of claim 1, wherein said substrate is configured as a retina implant.

8. The array of claim 7, wherein said retina implant is a subretinal implant.

9. The array of claim 7, wherein said retina implant is a subretinal implant being essentially permeable for visible light.

10. An optically controllable microelectrode array for stimulating cells within a tissue, the array comprising
    a substrate including at least one light-sensitive layer having a flat surface, said light-sensitive layer being adapted to switch at selected parts thereof to a potential for exerting an electrical stimulus when irradiated at said selected parts; and
    a plurality of at least 16 electrodes arranged on said flat surface;
    wherein selected ones of said electrodes in contact with said selected parts of said light-sensitive layer, when irradiated, exert electrical stimuli to cells exposed to said selected ones of said electrodes.

11. The array of claim 10, wherein said plurality of said electrodes on said flat surface comprises at least 256 electrodes exposed toward said tissue.

12. The array of claim 10, wherein said electrodes arranged on said flat surface are electrically isolated from each other.

13. The array of claim 11, wherein said electrodes arranged on said flat surface are electrically isolated from each other.

14. An assembly including a tissue formed by a plurality of biological cells and an optically controllable microelectrode array having a surface in contact with said tissue for stimulating said cells within said tissue, each said cell having a surface area exposed toward said surface, said array comprising:
    a substrate including at least one light-sensitive layer having a flat surface facing said tissue, said light-sensitive layer being adapted to switch at selected parts thereof to a potential exerting an electrical stimulus when irradiated at said selected parts; and
    a plurality of electrodes arranged on said flat surface exposed toward said tissue, each said electrode having a first surface area exposed toward said tissue and dimensioned such that said first surface is substantially smaller than the average surface area of said cells exposed toward said electrodes;
    wherein selected ones of said electrodes in contact with said selected parts of said light-sensitive layer, when irradiated, exert electrical stimuli to cells exposed toward said selected ones of said electrodes.

15. The array of claim 14, wherein said electrodes arranged on said flat surface are electrically isolated from each other.

16. The array of claim 10, wherein said substrate further comprises a semiconductor layer, said semiconductor layer and said microelectrodes forming light-sensitive switches for exerting stimuli to one of said cells in contact with said microelectrode, when irradiated with light impinging an said tissue.

17. The array of claim 15, wherein said plurality of said electrodes on said flat surface comprises at least 16 electrodes exposed toward said tissue.

18. The array of claim 15, wherein said plurality of said electrodes on said flat surface comprises at least 256 electrodes exposed toward said tissue.

19. The array of claim 14, wherein the ratio between said average surface area and said first surface area is between 5 and 10.

* * * * *

UNITED STATES PATENT AND TRADEMARK OFFICE
CERTIFICATE OF CORRECTION

PATENT NO. : 6,347,250 B1
DATED : February 12, 2002
INVENTOR(S) : Wilfried Nisch et al.

It is certified that error appears in the above-identified patent and that said Letters Patent is hereby corrected as shown below:

<u>Title page</u>,
Item [73], please insert Assignee as follows:
-- NMI Naturwissenschaftliches und Medizinisches Institut an der Universität Tübingen, Reutlingen Germany --
Item [74], *Attorney, Agent, or Firm*, please insert name of attorney as follows:
-- Burns, Doane, Swecker & Mathis LLP
   Claude A.S. Hamrick --

Signed and Sealed this

Second Day of March, 2004

JON W. DUDAS
*Acting Director of the United States Patent and Trademark Office*